United States Patent [19]

Crenshaw et al.

[11] 4,098,788

[45] Jul. 4, 1978

[54] PROCESS FOR PREPARING QUINAZOLINES

[75] Inventors: Ronnie Ray Crenshaw, Dewitt; George Michael Luke, Lafayette; Richard Anthony Partyka, Liverpool, all of N.Y.

[73] Assignee: Bristol-Myers Company, New York, N.Y.

[21] Appl. No.: 807,941

[22] Filed: Jun. 20, 1977

[51] Int. Cl.$^2$ ............................................ C07D 239/94
[52] U.S. Cl. ................................ 544/293; 260/553 A
[58] Field of Search ...................... 260/251 Q, 256.4 Q

[56] References Cited

U.S. PATENT DOCUMENTS

| | | | |
|---|---|---|---|
| 2,517,824 | 8/1950 | Appelquest | 260/256.4 Q |
| 3,511,836 | 5/1970 | Hess | 260/256.4 Q |
| 3,669,968 | 6/1972 | Hess | 260/256.4 Q |
| 3,920,636 | 11/1975 | Takahashi et al. | 260/256.4 Q |
| 4,001,237 | 1/1977 | Partyka et al. | 260/256.4 Q |
| 4,001,238 | 1/1977 | Partyka et al. | 260/256.4 Q |

OTHER PUBLICATIONS

Elderfield, Heterocyclic Compounds, vol. 6, pp. 328–358, pub. by Wiley & Sons, (1957).

*Primary Examiner*—Paul M. Coughlan, Jr.
*Attorney, Agent, or Firm*—Robert H. Uloth

[57] ABSTRACT

2-Halo-4-aminoquinazolines are produced by a two-step process involving cyclization of 1-phenyl-3-cyanoureas or 1-phenyl-3-cyanothioureas in the presence of phosphorus halides and phosphorus oxyhalides to provide a phosphoquinazoline intermediate which is hydrolyzed to the quinazoline. Exemplary of the process is the intramolecular cyclization of 1-(3,4-dimethoxyphenyl)-3-cyanourea in the presence of phosphorus pentachloride and phosphorus oxychloride to a phosphoquinazoline intermediate which is subsequently hydrolyzed with formic acid to 2-chloro-4-amino-6,7-dimethoxyquinazoline. The 2-halo-4-aminoquinazolines of the instant process are particularly valuable as intermediates in the preparation of 4-amino-2-(4-substituted-piperazin-1-yl)quinazolines useful in the treatment of cardiovascular disease, e.g. hypertension.

21 Claims, No Drawings

PROCESS FOR PREPARING QUINAZOLINES

FIELD OF THE INVENTION

This invention is concerned with a new process for the production of 2-halo-4-aminoquinazolines. These chemical compounds are utilized as intermediates in the preparation of antihypertensive agents such as the various 4-amino-2-(4-substituted piperazin-1-yl)quinazolines described in U.S. Pat. Nos. 3,511,836, 3,669,968, 4,001,237, 4,001,238 and the 2-(4-substituted homopiperazino)-4-amino-6,7-dimethoxyquinazolines of U.S. Pat. No. 3,920,636.

DESCRIPTION OF THE PRIOR ART

Hess U.S. Pat. No. 3,511,836 (patented May 12, 1970) discloses preparation of 2-chloro-4-aminoquinazolines by reaction of 2,4-dichloroquinoazlines with ammonia in a solvent such as tetrahydrofuran.

Hess U.S. Pat. No. 3,669,968 (patented June 13, 1972) describes a process for preparing 2-halo-4-amino-6,7,8-trialkoxy-quinazoline by treating 2,4-dihalo-6,7,8-trialkoxyquinazolines with ammonia in a reaction-inert organic solvent.

Takahashi, et al. U.S. Pat. No. 3,920,636 (patented November 18, 1975) described preparation of 1-(4-substituted homopiperazino)-4-amino-6,7-dimethoxyquinazolines from 2-chloro-4-amino-6,7-dimethoxyquinazolines.

Partyka, et al. U.S. Pat. Nos. 4,001,237 and 4,001,238 (both patented January 4, 1977) employ 2-chloro-4-amino-6,7-dimethoxyquinazoline as starting material in the preparation of a series of 6,7-dimethoxy-4-amino-2-(piperazinyl)quinazolines in which the piperazinyl radical is incorporated as the amine fragment of oxazole, isoxazole, thiazole, isothiazole and 1,2,4-oxadiazole amides.

SUMMARY OF THE INVENTION

Broadly described, this invention is concerned with a new process for preparation of 2-halo-4-aminoquinazolines of formula I

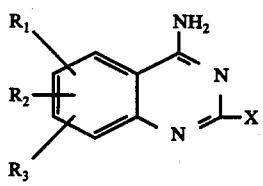

wherein X is a halogen atom selected from the group consisting of chlorine and bromine; $R_1$, $R_2$, are independently selected from the group consisting of hydrogen, lower alkyl and lower alkoxy radicals which involves intramolecular cyclization of 1-phenyl-3-cyanoureas or 1-phenyl-3-cyanothioureas in the presence of a mixture of phosphorus trichloride or phosphorus pentachloride and phosphorus oxychloride or a mixture of phosphorus tribromide or phosphorus pentabromide and phosphorus oxybromide to provide a quinazoline phosphorus intermediate that is subsequently hydrolyzed to the 2-halo-4-aminoquinazoline of formula I.

DETAILED DESCRIPTION OF THE INVENTION

As indicated hereinabove, the instant invention is concerned with a process for preparing compounds of formula I

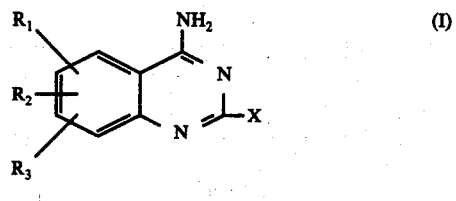

wherein
X is halogen selected from the group consisting of chlorine and bromine; and
$R_1$, $R_2$, and $R_3$ are independently selected from the group consisting of hydrogen, lower alkyl of 1 to 4 carbon atoms inclusive and lower alkoxy of 1 to 4 carbon atoms inclusive
which comprises the consecutive steps of
(a) treating a compound of formula II

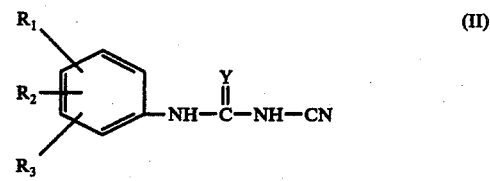

wherein $R_1$, $R_2$ and $R_3$ are as above and Y is oxygen or sulfur with a mixture of phosphorus halides and phosphorus oxyhalides selected from the group consisting of phosphorus trichloride or phosphorus pentachloride and phosphorus oxychloride, or phosphorus tribromide or phosphorus pentabromide and phosphorus oxybromide until the cyclization is essentially complete to provide a quinazoline phosphoramide intermediate;
(b) hydrolyzing said intermediates to produce the compound of formula I.

Preferred embodiments of the foregoing process for the preparation of compounds characterized by formula I are those wherein:
in step (a) the compound of formula II is a cyanourea wherein $R_1$, $R_2$ and $R_3$ are as above and Y is oxygen;
in step (a) the compound of formula II is a cyanothiourea wherein $R_1$, $R_2$ and $R_3$ are as above and Y is sulfur;
in step (a) the compound of formula II is 1-(3,4-dimethoxyphenyl)-3-cyanourea;
in step (a) the compound of formula II is 1-(2,3,4-trimethoxyphenyl)-3-cyanourea;
in step (a) the compound of formula II is 1-(3,4-dimethoxyphenyl)-3-cyanothiourea;
in step (a) the compound of formula II is 1-(2,3,4-trimethoxyphenyl)-3-cyanothiourea;
in step (a) a mixture of phosphorus pentachloride and phosphorus oxychloride is employed;
in step (a) a mixture of phosphorus pentabromide and phosphorus oxybromide is employed;
in step (a) the compound of formula II is treated with a mixture of a molar equivalent of phosphorus trichloride or phosphorus pentachloride and a solvent amount of phosphorus oxychloride;

in step (a), the compound of formula II is treated with a mixture of about a molar equivalent of phosphorus tribromide or phosphorus pentabromide and a solvent amount of phosphorus oxybromide;

step (a) is carried out with the aid of heat at a temperature in the range of about 23°–125°;

step (a) is carried out with the aid of heat at a temperature in the range of 85°–95°;

step (a) is carried out at a temperature in the range of 85°–95° for a period of 2 to 3 hours;

in step (b), the phosphoramide intermediate is hydrolyzed under acidic conditions to provide a quinazoline of formula I;

in step (b), the phosphoramide intermediate is hydrolyzed with dilute alkali to provide a quinazoline of formula I;

in step (b) the phosphoramide intermediate is hydrolyzed with formic acid to provide a quinazoline of formula I;

step (b) is carried out at a temperature in the range of 85°–95°;

step (b) is carried out at a temperature in the range of 85°–95° for a period of 5 to 15 minutes;

step (b) is carried out at a temperature in the range of 85°–95° for a period of 5 to 15 minutes and then cooled to a temperature in the range of 5°–15°.

Another preferred embodiment of the present invention is a process for the preparation of a quinazoline of formula III

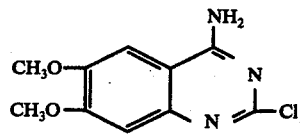
(III)

which comprises the consecutive steps of
(a) treating a cyanourea having formula IV

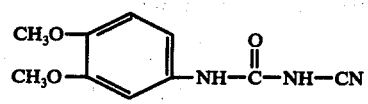
(IV)

with about a molar equivalent of a mixture of phosphorus trichloride or phosphorus pentachloride in a solvent amount of phosphorus oxychloride until cyclization is essentially complete to provide a quinazoline phosphoramide intermediate;

(b) hydrolyzing said intermediate with formic acid to produce the formula III compound.

Still another preferred embodiment of the present invention is a process for the preparation of a quinazoline of formula V

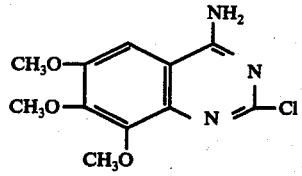
(V)

which comprises the consecutive steps of
(a) treating a cyanourea having formula VI

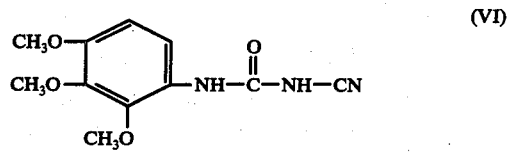
(VI)

with about a molar equivalent of a mixture of phosphorus trichloride or phosphorus pentachloride in a solvent amount of phosphorus oxychloride until cyclization is essentially complete to provide a quinazoline phosphoramide intermediate;

(b) hydrolyzing said intermediate with formic acid to produce the formula V compound.

According to the general process of this invention, cyanoureas and cyanothioureas of formula II are intramolecularly cyclized to a phosphoquinazoline intermediate which is then hydrolyzed to provide quinazoline compounds characterized by formula I. Cyclization of a formula II urea to the phosphoquinazoline intermediate is conveniently carried out by reacting the urea with a mixture of phosphorus trichloride or phosphorus pentachloride and phosphorus oxychloride. While the exact chemical identity of the cyclized organophosphorus intermediate has not been unequivocally proved, it is believed to be a phosphoramido compound in which the 4-amino substituent of the 2-chloroquinazoline is incorporated in the phosphoramide. Approximately equimolar portions of a mixture of phosphorus trichloride or phosphorus pentachloride and the formula II urea with a convenient solvent amount of phosphorus oxychloride relative to the amount of urea starting material are employed. Commonly used temperatures for carrying out the cyclization reaction range from about 25°–125°, and a particularly preferred temperature range is from about 85°–95°. As will be appreciated by those skilled in the art, the reaction time and conditions needed for the cyclization of the compounds of formula II vary according to several factors. For instance, at lower temperatures, longer reaction periods are needed while at higher temperatures the cyclization reaction is completed in a shorter time. Reaction times of from about 1 to 12 hours can be used with a period of 2 to 3 hours preferred at temperatures in the range of about 85°–95°.

When the cyclization of a formula II urea is carried out according to the procedure described above with phosphorus tribromide or phosphorus pentabromide and phosphorus oxybromide rather than the corresponding "phosphochlorides", the 2-bromo-4-aminoquinazoline phosphoramido intermediate is obtained.

The quinazoline compounds characterized by formula I are obtained from the 2-haloquinazoline phosphoramide intermediates by hydrolytic conditions generally employed in cleavage of phosphorus-nitrogen bonds of phosphoramides. This particular reaction can be carried out under acidic conditions employing acids such as acetic or hydrochloric acid in varying concentrations or with dilute aqueous alkali such as sodium hydroxide, potassium hydroxide, sodium carbonate and the like. As will be evident to those skilled in the art, reaction conditions for carrying out the hydrolysis must be strong enough to hydrolyze the phophorus-nitrogen bond yet mild enough to ensure that the "2-halo" or "4-amino" functionalities remain intact. In this regard, a preferred hydrolysis method involves addition of the phosphoramido intermediate to formic acid (preferably at a concentration of 10 to 20%) at a temperature within the range of about 40°–60° and then completing the reaction by heating to about 85°–95° for a period of 5 to 15 minutes followed by cooling to a temperature of 5°–15°. Hydrolyis of the 2-haloquinazoline phosphoramido intermediate is time and temperature dependent with respect to optimizing yields. For instance, considerable unchanged phosphoramide intermediate remains at temperatures below 85° and, if the reaction mixture is heated substantially longer than 5–15 minutes, the yield of the desired 2-halo-4-aminoquinazolines is appreciably diminished. The 2-halo-4-aminoquinazolines of formula I generally spontaneously precipitate from the cooled reaction mixture as a mixture of the base and hydrochloride or hydrobromide salt and are recovered by simple filtration in yields of 80% or greater.

The mixture of 2-halo-4-aminoquinazoline and salt form thereof can be converted to the pure quinazoline base form by conventional procedures; for instance, by treating the mixture with a base such as triethylamine. Complete conversion to the base form is not required when the 2-halo-4-aminoquinazoline of formula I are employed as starting materials in the preparation of quinazoline antihypertensive agents. For instance, reaction of a mixture of 2-chloro-4-amino-6,7-dimethoxyquinazoline and hydrochloride salt thereof with 1-(5-methylthio-1,3,4-oxadiazole-2-carbonyl)-piperazine hydrochloride in the presence of base according to the procedure described in U.S. Pat. No. b 4,001,238 provides 4-amino-6,7-dimethoxy-2-[4-(5-methylthio-1,3,4-oxadiazole-2-carbonyl)piperazin-1-yl]quinazoline.

The cyanoureas and cyanothioureas of formula II employed as starting material in the process of the present invention, such as 1-(3,4-dimethoxyphenyl)-3-cyanourea, 1-(2,3,4-trimethoxyphenyl)-3-cyanourea and corresponding thioureas, are prepared by treating the appropriate phenylisocyanate or phenylisothiocyanate with cyanamide and sodium hydroxide according to the general procedure of F. Kurzer, et al., Org. Syn., Coll. Vol. IV, page 213. Another embodiment of the instant invention constitutes the compounds of formula II in which Y is oxygen or sulfur and $R_1$, $R_2$ and $R_3$ are limited to lower alkyl of 1 to 4 carbon atoms inclusive or lower alkoxy of 1 to 4 carbon atoms inclusive.

In connection with the use herein of the term "solvent amount", it is to be understood that said term refers to a quantity of phosphorus oxychloride or phosphorus oxybromide sufficient to provide good mixing and handling characteristics with respect to the reaction mixture. For this purpose, a ratio of from about 2 to 15 ml. of phosphorus oxychloride or phosphorus oxybromide for each gram of the urea reactant of formula II is generally preferred.

It is to be understood that by the terms "lower alkyl" and "lower alkoxy", as used herein, it is meant that the carbon chain which comprises these groups include both straight and branched carbon radicals of 1 to 4 carbon atoms inclusive. Exemplary of these carbon chain radicals are methyl, ethyl, propyl, isopropyl, 1-butyl, 1-methylpropyl, 2-methylpropyl, and tert.-butyl.

By the term "independently selected", as used herein, it is meant that the $R_1$, $R_2$ and $R_3$ substituents may or may not be identical.

The following examples further illustrate the present invention and will enable others skilled in the art to understand it more completely. It is to be understood that the invention is not limited solely to the particularly examples given below. All temperatures expressed herein are in degrees centigrade.

EXAMPLE 1

1-(3,4-Dimethoxyphenyl)-3-cyanourea

Aqueous sodium hydroxide (5 ml., 3N) is added to a solution of cyanamid (1.68 g., 0.04 mole) in 5 ml. of water. After cooling the basic solution to 15°, 3,4-dimethoxyphenylisocyanate (3.58 g., 0.02 mole) obtained according to the procedure of Z. Budesinsky, et al., Collection Czech. Chem. Commun., 37, 2779 (1972), is added portion-wise with stirring over a 15 minute period with temperature maintained at 20°–25°. After the addition of about ½ of the isocyanate, a second 5.0 ml. portion of aqueous 3N sodium hydroxide is added to keep the mixture strongly alkaline throughout the reaction. After completing the isocyanate addition, the reaction mixture is stirred at 24° for 10 minutes, diluted with 4.0 ml. of water and filtered. The filtrate, cooled to 18° and acidified to a pH of approximately 3 with concentrated hydrochloric acid, provides 4.36 g. (99% yield) of 1-(3,4-dimethoxyphenyl)-3-cyanourea, m.p. 148°–152° (dec.). Analytically pure material is obtained by crystallization from acetonitrile, m.p. 152°–155° (dec.).

Analysis. Calcd. for $C_{10}H_{11}N_3O_3$ (percent): C, 54.30; H, 5.01; N, 19.00. Found (percent): C, 54.57; H, 5.10; N, 19.29.

EXAMPLE 2

2-Chloro-4-amino-6,7-dimethoxyquinazoline

Phosphorus pentachloride (7.15 g., 0.0344 mole) is added with stirring to 114 ml. of phosphorus oxychloride followed in 5 minutes by 1-(3,4-dimethoxyphenyl)-3-cyanourea (7.60 g., 0.0344 mole). The mixture is stirred at 25° for 15 minutes and then at 90°–92° for a period of 2.5 hours. After cooling, excess phosphorus oxychloride is first removed under reduced pressure and the resulting yellow powdery residue then stirred with an ice water mixture for 15 minutes and then filtered. The filter cake washed with water and dried under reduced pressure affords 11.67 g. of the quniazoline phosphoramido ester as a bright yellow solid. The phosphoramido ester (8.79 g., 0.0247 mole) is added at 50° to 175 ml. of 15% formic acid with stirring. This mixture is rapidly heated to 85°–95° where it is maintained for a period of 8–10 minutes and then cooled to 10° in an ice bath. The solid thus obtained is collected, washed with water and dried to provide 4.77 g. (81%) of 2-chloro-4-amino-6,7-dimethoxyquinazoline as a mixture of base and hydrochloride salt which is converted to the free base by treating with triethylamine yielding pure 2-chloro-4-amino-6,7-dimethoxyquinazoline, m.p. >300°.

Analysis. Calcd. for $C_{10}H_{10}ClN_3O_2$ (percent): C, 50.12; H, 4.21; N, 17.53; Cl, 14.79. Found (percent): C, 50.04; H, 4.19; N, 17.71; Cl, 14.50.

According to infrared, nuclear magnetic resonance, and high pressure liquid chromatography, the title quinazoline is identical with a sample prepared by treatment of 2,4-dichloroquinazoline with ammonia in tetrahydrofuran as described in U.S. Pat. No. 3,663,706.

When the above procedure is repeated employing an equimolar amount of 1-(3,4-dimethoxyphenyl)-3-cyanothiourea for 1-(3,4-dimethoxyphenyl)-3-cyanourea, the title compound "2-chloro-4-amino-6,7-dimethoxyquinazoline" is produced.

EXAMPLE 3

Following the procedure of Example 1 but employing an equimolar amount of phenylisocyanates listed below:
phenylisocyanate,
2-methylphenylisocyanate,
3-methylphenylisocyanate,
4-methylphenylisocyanate,
3-n-butylphenylisocyanate,
4-isopropylphenylisocyanate,
2,4-dimethylphenylisocyanate,
3,4-dimethylphenylisocyanate,
2,3,4-trimethylphenylisocyanate,
2-methoxyphenylisocyanate,
3-methoxyphenylisocyanate,
3-methoxyphenylisocyanate,
4-methoxyphenylisocyanate,
3-n-butoxyphenylisocyanate,
4-isopropoxyphenylisocyanate,
2,4-dimethoxyphenylisocyanate,
2,3,4-trimethoxyphenylisocyanate,
in place of 3,4-dimethoxyphenylisocyanate, there is produced, respectively,
(a) 1-(phenyl)-3-cyanourea,
(b) 1-(2-methylphenyl)-3-cyanourea,
(c) 1-(3-methylphenyl)-3-cyanourea,
(d) 1-(4-methylphenyl)-3-cyanourea,
(e) 1-(3-n-butylphenyl)-3-cyanourea,
(f) 1-(4-isopropylphenyl)-3-cyanourea,
(g) 1-(2,4-dimethylphenyl)-3-cyanourea,
(h) 1-(3,4-dimethylphenyl)-3-cyanourea,
(i) 1-(2,3,4-trimethylphenyl)-3-3cyanourea,
(j) 1-(2-methoxyphenyl)-3-cyanourea,
(k) 1-(3-methoxyphenyl)-3-cyanourea,
(l) 1-(4-methoxyphenyl)-3-cyanourea,
(m) 1-(3-n-butoxyphenyl)-3-cyanourea,
(n) 1-(4-isopropoxyphenyl)-3-cyanourea,
(o) 1-(2,4-dimethoxyphenyl)-3-cyanourea,
(p) 1-(2,3,4-trimethoxyphenyl)-3-cyanourea.

EXAMPLE 4

Following the procedure of Example 2 but employing an equmolar amount of the cyanoureas listed below:
1-(phenyl)-3-cyanourea,
1-(2-methylphenyl)-3-cyanourea,
1-(3-methylphenyl)-3-cyanourea,
1-(4-methylphenyl)-3-cyanourea,
1-(3-n-butylphenyl)-3-cyanourea,
1-(4-isopropylphenyl)-3-cyanourea
1-(2,4-dimethylphenyl)-3-cyanourea,
1-(3,4-dimethylphenyl)-3-cyanourea,
1-(2,3,4-trimethylphenyl)-3-cyanourea,
1-(2-methoxyphenyl)-3-cyanourea,
1-(3-methoxyphenyl)-3-cyanourea,
1-(4-methoxyphenyl)-3-cyanourea,
1-(3-n-butoxyphenyl)-3-cyanourea,
1-(4-isopropoxyphenyl)-3-cyanourea,
1-(2,4-dimethoxyphenyl)-3-cyanourea,
1-(2,3,4-trimethoxyphenyl)-3-cyanourea
in place of 1-(3,4-dimethoxyphenyl)-3-cyanourea, there is produced:
(a) 2-chloro-4-aminoquinazoline,
(b) 2-chloro-4-amino-8-methylquinazoline,
(c) 2-chloro-4-amino-7-methylquinazoline,
(d) 2-chloro-4-amino-6-methylquinazoline,
(e) 2-chloro-4-amino-7-n-butylquinazoline,
(f) 2-chloro-4-amino-6-isopropylquinazoline,
(g) 2-chloro-4-amino-6,8-dimethylquinazoline,
(h) 2-chloro-4-amino-6,7-dimethylquinazoline,
(i) 2-chloro-4-amino-6,7,8-trimethylquinazoline,
(j) 2-chloro-4-amino-8-methoxyquinazoline,
(k) 2-chloro-4-amino-7-methoxyquinazoline,
(l) 2-chloro-4-amino-6-methoxyquinazoline,
(m) 2-chloro-4-amino-7-n-butoxyquinazoline,
(n) 2-chloro-4-amino-6-isopropoxyquinazoline,
(o) 2-chloro-4-amino-6,8-dimethoxyquinazoline,
(p) 2-chloro-4-amino-6,7,8-trimethoxyquinazoline.

EXAMPLE 5

1-(3,4-Dimethoxyphenyl)-3-cyanothiourea

The title compound is produced by following the procedure of Example 1 but employing an equimolar amount of 3,4-dimethoxyphenylisothiocyanate in place of 3,4-dimethoxyphenylisocyanate.

EXAMPLE 6

2-Bromo-4-amino-6,7-dimethoxyquinazoline

The title compound is obtained by reacting 1-(3,4-dimethoxyphenyl)-3-cyanourea with phosphorous pentabromide in a solvent amount of phosphorous oxybromide according to the procedure of Example 2.

What is claimed is:

1. A process for preparing compounds of formula I

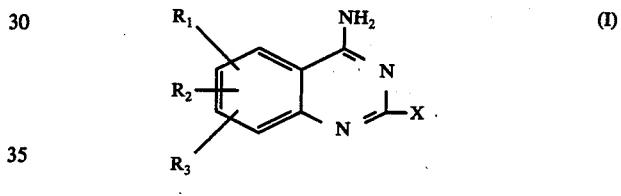

wherein
X is halogen selected from the group consisting of chlorine and bromine; and
$R_1$, $R_2$ and $R_3$ are independently selected from the group consisting of hydrogen, lower alkyl of 1 to 4 carbon atoms inclusive and lower alkoxy of 1 to 4 carbon atoms inclusive;
which comprises the consecutive steps of
(a) treating a compound of formula II

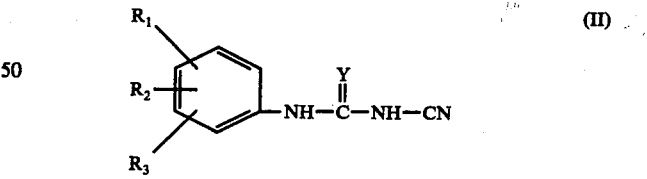

wherein $R_1$, $R_2$ and $R_3$ are as above and Y is oxygen or sulfur with a mixture of phosphorus halides and phosphorus oxyhalides selected from the group consisting of phosphorus trichloride or phosphorus pentachloride and phosphorus oxychloride, or phosphorus tribromide or phosphorus pentabromide and phosphorus oxybromide until the cyclization is essentially complete to provide a quinazoline phosphoramide intermediate;
(b) hydrolyzing said intermediate to produce the compound of formula I.

2. The process of claim 1 wherein in step (a) the cyanourea employed is a compound of formula II in which Y is oxygen.

3. The process of claim 1 wherein in step (a) the cyanothiourea employed is a compound of formula II in which Y is sulfur.

4. The process of claim 1 wherein in step (a) the compound of formula II employed is 1-(3,4-dimethoxyphenyl)-3-cyanourea.

5. The process of claim 1 wherein in step (a) the compound of formula II employed is 1-(2,3,4-trimethoxyphenyl)-3-cyanourea.

6. The process of claim 1 wherein in step (a) the compound of formula II employed is 1-(3,4-dimethoxyphenyl)-3-cyanothiourea.

7. The process of claim 1 wherein in step (a) the compound of formula II employed is 1-(2,3,4-trimethoxyphenyl)-3-cyanothiourea.

8. The process of claim 1 wherein in step (a) a mixture of phosphorus pentabromide and phosphorus oxybromide is employed.

9. The process of claim 1 wherein in step (a) a compound of formula II is treated with a mixture of a molar equivalent of phosphorus trichloride or phosphorus pentachloride and a solvent amount of phosphorus oxychloride.

10. The process of claim 1 wherein in step (a) the compound of formula II is treated with a mixture of about a molar equivalent of phosphorus tribromide or phosphorus pentabromide and a solvent amount of phosphorus oxybromide.

11. The process of claim 1 wherein step (a) is carried out with the aid of heat at a temperature in the range of about 25°-125°.

12. The process of claim 1 wherein step (a) is carried out with the aid of heat at a temperature in the range of 85°-95°.

13. The process of claim 1 wherein step (a) is carried out at a temperature in the range of 85°-95° for a period of 2-3 hours.

14. The process of claim 1 wherein in step (b) the phosphoramide intermediate is hydrolyzed under acidic conditions to provide a quinazoline of formula I.

15. The process of claim 1 wherein in step (b) the phosphoramide intermediate is hydrolyzed with dilute alkali to provide a quinazoline of formula I.

16. The process of claim 1 wherein in step (b) the phosphoramide intermediate is hydrolyzed with formic acid to provide a quinazoline of formula I.

17. The process of claim 1 wherein step (b) is carried out at a temperature in the range of 85°-95°.

18. The process of claim 1 wherein step (b) is carried out at a temperature in the range of 85°-95° for a period of 5-15 minutes.

19. The process of claim 1 wherein step (b) is carried out at a temperature in the range of 85°-95° for a period of 5-15 minutes and then cooled to a temperature in the range of 5-15°.

20. A process for the preparation of a quinazoline of formula III

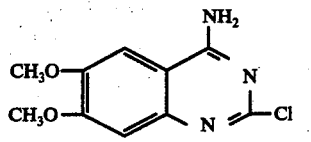

which comprises the consecutive steps of
(a) treating a cyanourea having formula IV

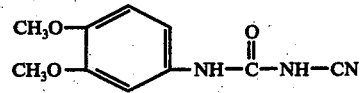

with about a molar equivalent of a mixture of phosphorus trichloride or phosphorus pentachloride in a solvent amount of phosphorus oxychloride until cyclization is essentially complete to provide a quinazoline phosphoramide intermediate;
(b) hydrolyzing said intermediate with formic acid to produce the formula III compound.

21. A process for the preparation of a quinazoline of formula V

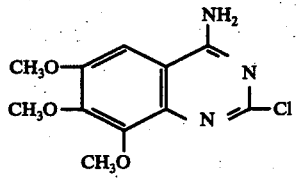

which comprises the consecutive steps of
(a) treating a cyanourea having formula VI

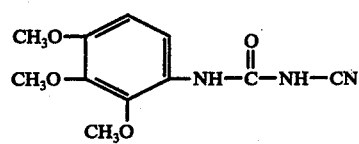

with about a molar equivalent of a mixture of phosphorus trichloride or phosphorus pentachloride in a solvent amount of phosphorus oxychloride until cyclization is essentially complete to provide a quinazoline phosphoramide intermediate;
(b) hydrolyzing said intermediate with formic acid to produce the formula V compound.

* * * * *